United States Patent [19]

Byrd

[11] Patent Number: 5,797,851
[45] Date of Patent: Aug. 25, 1998

[54] MEDICAL BLADDER COVER

[76] Inventor: Timothy N. Byrd, P.O. Box 490, Townsend, Tenn. 37882

[21] Appl. No.: 801,757

[22] Filed: Feb. 18, 1997

[51] Int. Cl.⁶ .................................................. A61B 5/00
[52] U.S. Cl. .................................... 600/499; 606/202
[58] Field of Search ........................ 606/201.4; 600/499

[56] References Cited

U.S. PATENT DOCUMENTS

| | | | |
|---|---|---|---|
| 2,244,871 | 6/1941 | Guinzburg | 2/59 |
| 2,911,974 | 11/1959 | Spence | 128/293 |
| 2,949,914 | 8/1960 | Waldrum | 128/402 |
| 3,473,525 | 10/1969 | Hanafin | 128/2.05 |
| 4,197,944 | 4/1980 | Catlin | 206/306 |
| 4,406,281 | 9/1983 | Hubbard et al. | 128/132 R |
| 4,458,249 | 7/1984 | Slaughterbeck | 150/52 R |
| 4,549,550 | 10/1985 | Kami | 128/686 |
| 4,572,173 | 2/1986 | Comeau | 128/132 D |
| 4,727,885 | 3/1988 | Ruff | 128/686 |
| 4,905,715 | 3/1990 | Johnson | 128/882 |
| 4,911,151 | 3/1990 | Rankin et al. | 128/82 |
| 4,967,758 | 11/1990 | Masciarotte | 128/686 |
| 4,979,953 | 12/1990 | Spence | 606/202 |
| 5,201,758 | 4/1993 | Glover | 606/202 |
| 5,228,448 | 7/1993 | Byrd | 128/677 |
| 5,411,518 | 5/1995 | Goldstein et al. | 128/686 |
| 5,513,643 | 5/1996 | Suite | 128/686 |
| 5,620,001 | 4/1997 | Byrd et al. | 128/686 |

FOREIGN PATENT DOCUMENTS 15450  11/1887  United Kingdom .

*Primary Examiner*—Robert L. Nasser
*Attorney, Agent, or Firm*—Pitts & Brittian, P.C.

[57] ABSTRACT

A medical bladder cover (10) for releasably securing a medical bladder (22) to a patient and for providing a protective covering around the medical bladder. The bladder cover (10) includes a body (12) having an elongated portion (14) for being releasably received around an appendage of a patient. A bladder engaging portion is defined by the elongated portion (14) of the body (12) for releasably engage a medical bladder (22). The body (12) of the medical bladder cover also includes a flap portion (20) secured to the elongated portion (14) of the body (12) for being folded over the medical bladder (22) as the elongated portion (14) engages the medical bladder. At least one adhesive surface portion (24) is provided on the bladder engaging portion of the elongated portion (14) of the body (12) for releasably bonding the bladder engaging portion to the medical bladder. Also provided is a mechanism for releasably securing the elongated portion (14) of the body about an appendage of the patient.

11 Claims, 5 Drawing Sheets

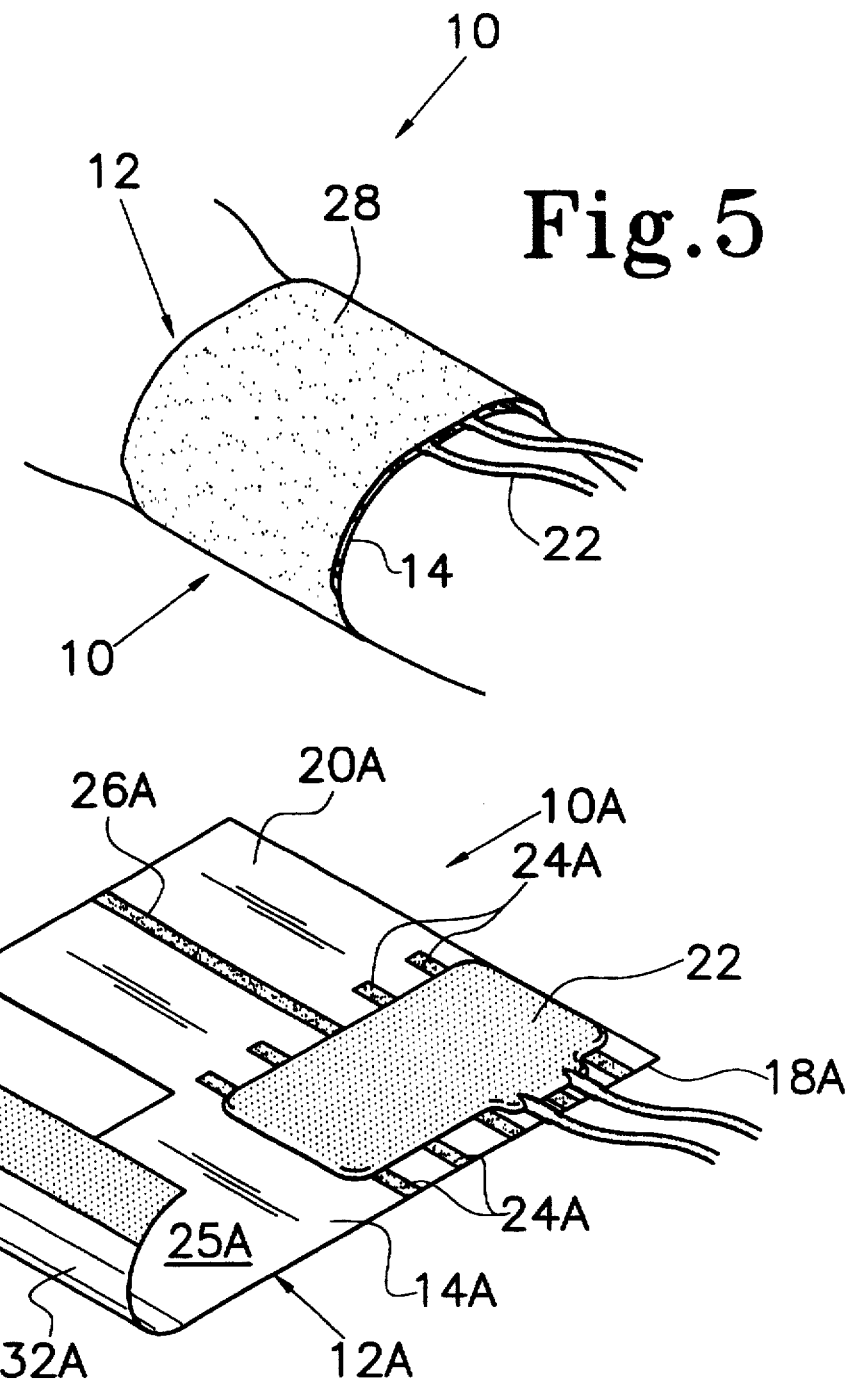

5,797,851

1

MEDICAL BLADDER COVER

TECHNICAL FIELD

This invention relates to a protective cover for a medical bladder, such as a sphygmomanometer bladder, which releasably secures the bladder to a patient and which prohibits contaminants from being communicated between the bladder and the patient. In this particular invention the bladder cover includes a body fabricated of flexible sheet material, with the body defining an elongated portion for being releasably received around an appendage of the patient and for engaging a medical bladder, and defining a flap portion for being folded over the medical bladder as the elongated portion engages the medical bladder.

BACKGROUND ART

Sphygmomanometers have long been used for monitoring the blood pressure of a patient. Such devices generally include a bladder provided with a permanent cover so as to define a sphygmomanometer cuff for being received about an appendage of the patient. It is known in the medical community that significant bacterial colonization occurs on surfaces of non-disposable sphygmomanometer cuffs, more commonly referred to as blood-pressure cuffs, as well as on reused disposable cuffs. Contamination of blood-pressure cuffs can be particularly problematic in hospital intensive care units and emergency rooms where the cuffs are commonly exposed to blood and other bodily fluids, thus making the cuffs a possible source of infection if reused. With the increasing recognition that contamination of blood-pressure cuff can be a source of infection, it has been recommended that, where possible, a sterilized cuff, or an unused disposable cuff, be dedicated to each patient upon arrival at a hospital and that the cuff follow the patient around in the hospital. However, dedicating a cuff to each patient requires a large number of cuffs, thereby making the practice expensive. Moreover, it is procedurally difficult to insure that the cuff follows the patient's movements in the hospital. Disposable cuffs are available as a possible solution, but disposable cuffs also lead to substantial additional expense. Consequently persons working in the medical field still commonly reuse blood-pressure cuffs on different patients without cleaning the cuffs between patients.

In U.S. Pat. No. 5,228,448 ("the '448 Patent) a protective cover for a blood-pressure cuff is disclosed which reduces the possibility of contaminates being transmitted between a blood-pressure cuff and a patient. The protective cover of this patent includes a protective sheet defining an elongated bottom band joined by an intermediate portion to an elongated top band. The bottom band is wrapped about the appendage of a patient, and the blood-pressure cuff is wrapped about the bottom band. The top band is then pivoted relative to the bottom band at the intermediate portion over the blood-pressure cuff and wrapped thereabout. Whereas the cover of the '448 Patent represented a considerable advancement of the art, with this protective cover contaminates can still be communicated between the patient and cuff at the opposite edges of the cover. For example, where a patient is loosing blood or other bodily fluids the cover does not prevent such fluids from being communicated between the top and bottom bands at the edges of such bands. The cover of the '448 patent also restricts the positioning of the pneumatic tubes which communicate with the gauge and pump of the sphygmomanometer, and due to the manner in which such tubes exit the cover, movement of the patient can result in the cover being pulled out of position. Further, if the top band of the cover is tightly secured over the cuff so as to most advantageously prevent contamination of the cuff it can interfere with the proper inflation of the cuff and cause inaccurate blood pressure readings.

Other covering devices are shown in U.S. Pat. Nos. 5,201,758; 4,979,953; 4,967,758; 4,911,151; 4,905,715; 4,572,173; 4,549,550; 4,548,249; 4,406,281; 4,378,009; 4,197,944; 3,473,525; 2,949,914; 2,911,974; 2,244,871 and 15,450.

As the art cited above reflects, heretofore protective covers have been used to cover the entire sphygmomanometer cuff. This approach results in the use of both a permanent cover and a removable or disposable cover over the sphygmomanometer bladder, the bladder being the operative element which must be protected from contamination. This duplication of protective coverings leads to unnecessary cost and can make the sphygmomanometer cuff a bulk or uncomfortable apparatus to use.

Therefore, it is an object of the present invention to provide medical bladder cover which prohibits contaminates from being communicated between a patient and a medical bladder, such as a sphygmomanometer bladder used for monitoring blood pressure.

It is an object of the present invention to provide an improved bladder cover which protects health care workers from coming into contact with contaminated blood-pressure cuffs.

Yet another object of the present invention is to provide a bladder cover which does away with the need for both a permanent and removable cover, and which is easy to use and inexpensive to manufacture.

Still another object of the present invention is to provide a bladder cover which does not affect the accuracy of a sphygmomanometer.

SUMMARY OF THE INVENTION

Other objects and advantages will be accomplished by the present invention which provides a medical bladder cover for releasably securing a medical bladder to a patient and for providing a protective covering around the medical bladder. The bladder cover includes a body fabricated of flexible sheet material. The body has an elongated portion for being releasably received around an appendage of a patient, and a bladder engaging portion is defined by the elongated portion for releasably engage a medical bladder. The body of the medical bladder cover also includes a flap portion secured to the elongated portion of the body for being folded over the medical bladder as the elongated portion engages the medical bladder. A mechanism is provided for releasably securing the body of the bladder cover to the medical bladder, the mechanism including at least one first adhesive surface portion provided on the bladder engaging portion of the elongated portion of the body for releasably bonding the body to the medical bladder. Also provided is a mechanism for releasably securing the elongated portion of the body about an appendage of the patient.

BRIEF DESCRIPTION OF THE DRAWINGS

The above mentioned features of the invention will be more clearly understood from the following detailed description of the invention read together with the drawings in which:

FIG. 5 illustrates a perspective view of a bladder cover of the present invention as it is received about an appendage of a patient.

FIG. 6 illustrates a perspective view of a first alternate embodiment of the bladder cover of the present invention.

BEST MODE FOR CARRYING OUT THE INVENTION

Figure 1:
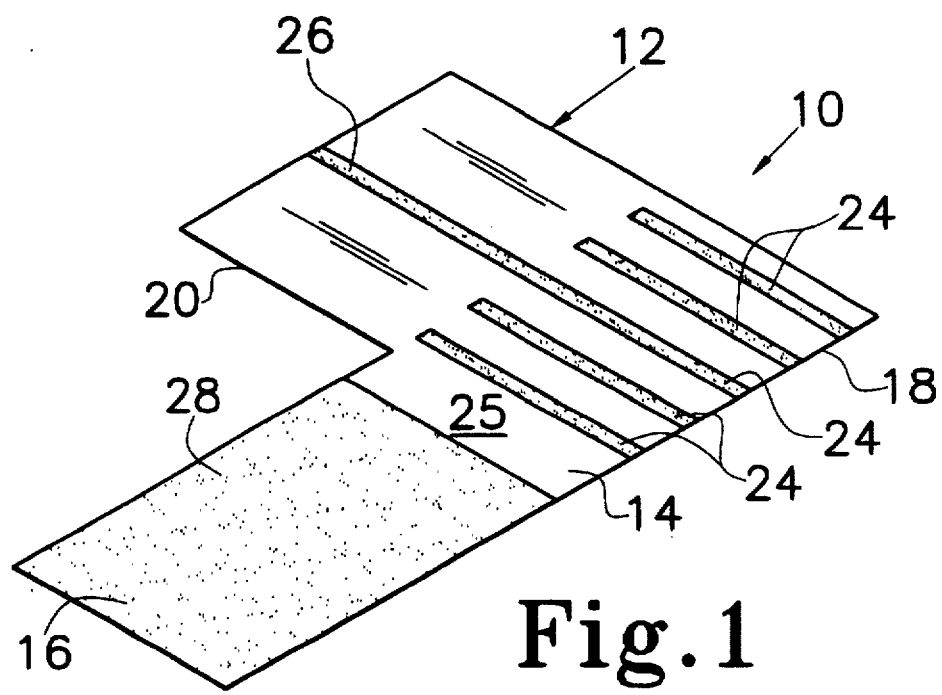
FIG. 1 illustrates a perspective view of a bladder cover of the present invention prior to installation of a medical bladder.

A medical bladder cover incorporating various features of the present invention is illustrated generally at 10 in FIGS. 1–5. The protective cover 10 is designed to cover a medical bladder, such as a sphygmomanometer bladder utilized for measuring the blood-pressure of a patient, and to releasably secure such bladder to a patient. The cover 10 serves to prevent the bladder from becoming contaminated during use and/or to protect the patient from being contaminated by the bladder. It will be recognized by those skilled in the art that during the blood-pressure measuring process such sphygmomanometer bladders are typically housed in permanent protective coverings to form sphygmomanometer cuffs which are releasably received about a patient's appendage, such as a patient's arm. As is set forth in detail below the protective cover 10 of the present invention replaces the conventional permanent covering of the cuff, and places a removable/replaceable protective layer of material about the bladder such that contaminates are prevented from contacting the bladder, and such that the bladder does not come into direct contact with the patient. Whereas in the discussion below the bladder cover 10 is discussed in terms of covering a sphygmomanometer bladder, it will be recognized that the cover 10 can be used to cover various medical bladders which are releasably secured to a patient.

In the embodiment illustrated in FIGS. 1–5, the bladder cover 10 includes a body 12 fabricated of a flexible sheet material. One suitable sheet material is spun bond polypropylene, but various flexible materials can be used. The body defines an elongated portion 14 having first and second end portions 16 and 18, respectively. A flap portion 20 extends outwardly from an edge of the elongated portion 14. In the preferred illustrated embodiment of FIGS. 1–5 the flap portion 20 extends laterally from the edge of the elongated portion 14 proximate the second end portion 18 of the elongated portion 14 such that the body defines an L-shaped configuration. Also, in the preferred embodiment, the flap portion 20 is integrally formed with the elongated portion 14. However, it will be appreciated that the flap portion 20 can be a separate element which is either permanently, or releasably, secured to the elongated portion 14.

Figure 2:
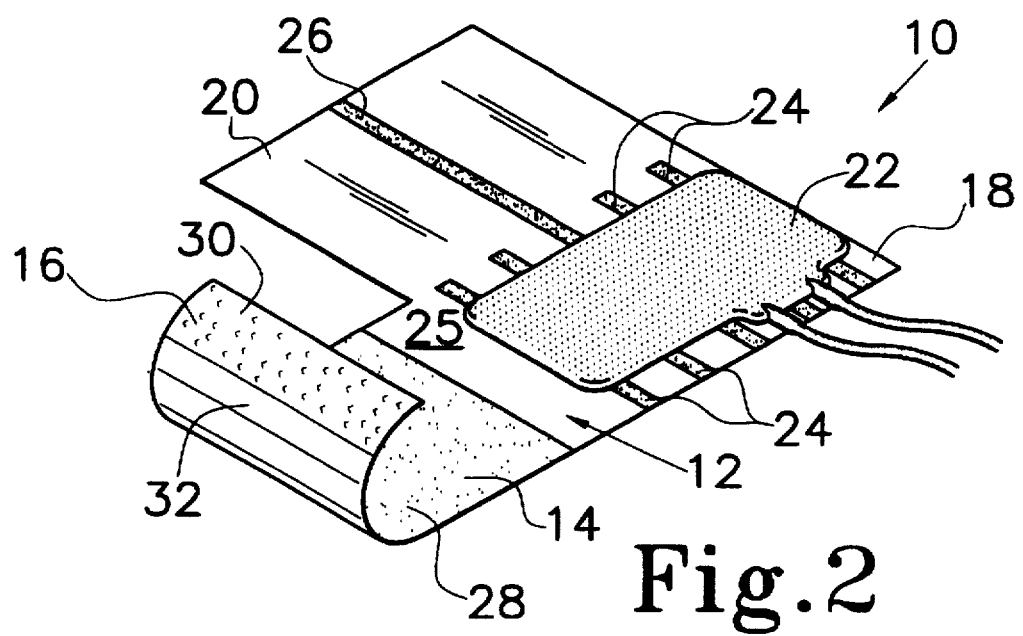
FIG. 2 illustrates a perspective view of a bladder cover of the present invention with a medical bladder engaging the body of the bladder cover.

As illustrated in FIG. 2, the second end portion 18 of the elongated portion 14 engages one of the sides of a medical bladder 22 during use. In this regard, a mechanism is provided for releasably securing the second end portion 18 of the elongated portion 14 to the bladder 22. In the preferred embodiment such mechanism includes at least one, and preferably a plurality of, adhesive surface portions 24 provided on a first surface 25 of the elongated portion 14 proximate the second end portion 18. Accordingly, when the cover 10 is prepared for use, the bladder 22 is positioned on the second end portion 18 so as to engage the adhesive surface portions 24 thereby securing the body 12 to the bladder 22.

Figure 3:
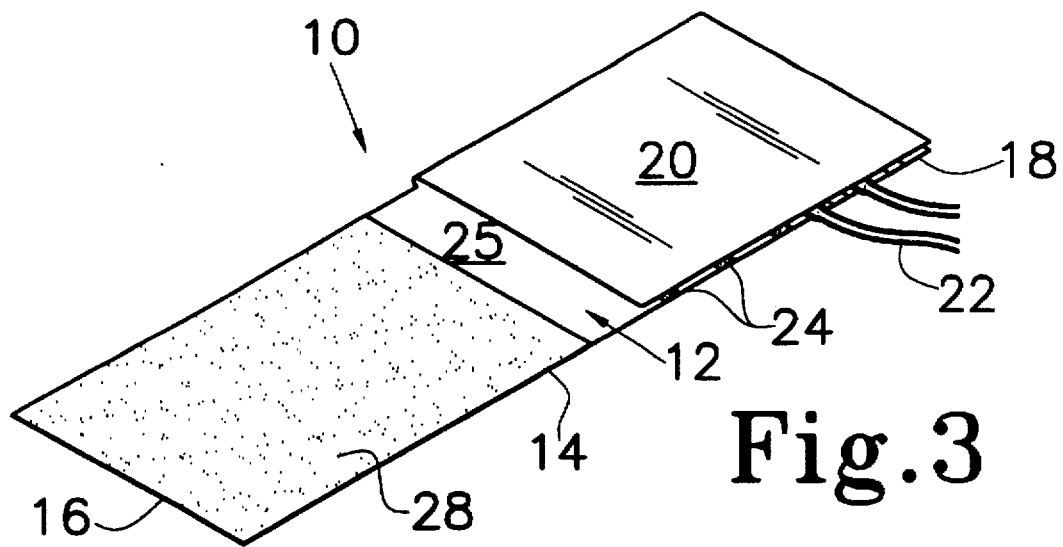
FIG. 3 illustrates a perspective view of a bladder cover of the present invention with a medical bladder engaging the body of the bladder cover.
Figure 4:
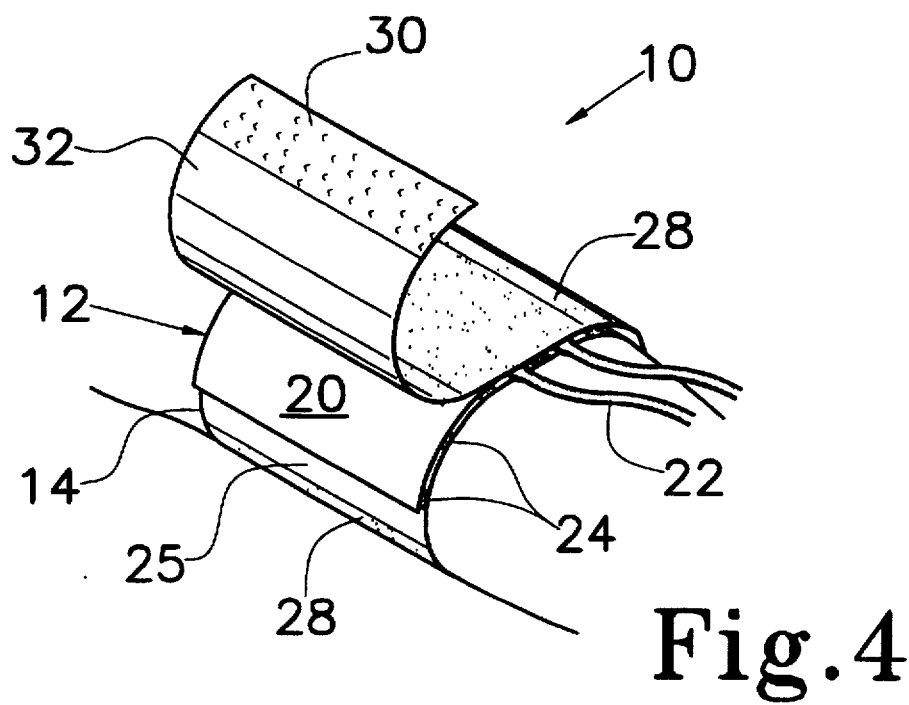
FIG. 4 illustrates a perspective view of a bladder cover of the present invention as it is received about an appendage of a patient.

As illustrated in FIGS. 3 and 4, after the second end portion 18 of the elongated portion 14 of the body 12 is secured to the bladder 22, the flap portion 20 is folded over the bladder 22 and over the second end portion 18 so as to form a protective cover over the bladder 22. It will be recognized that by pressing the flap portion 20 into contact with the adhesive surface portions 24 about the perimeter of the bladder 22 the flap portion 20 is releasably held in place with the bladder 22 secured between the elongated portion 14 and the flap portion 20. However, in the preferred embodiment, at least one further adhesive surface portion 26 is provided on the surface of the flap portion 20 for releasably engaging the bladder 22 when the flap portion 20 is folded over into position.

A mechanism is also provided for releasably securing the elongated portion 14 of the body 12 about an appendage of a patient. In one preferred embodiment such mechanism includes a hook and loop fastener having a loop component 28 and a hook component 30. The loop component 28 is disposed on the first surface 25 of the elongated portion 14 and covers at least a substantial portion of the first end portion 16 of the elongated portion 14 of the body 12. The hook component 30 is disposed on the second surface 32 proximate the first end portion 16 of the elongated portion 14. Accordingly, after the bladder 22 has been positioned between the elongated portion 14 and the flap portion 20, the body 12 can be wrapped around the arm, or other appendage, of the patient as illustrated in FIG. 4. When the body 12 is wrapped sufficiently tight around the arm, the hook component 30 is placed in engagement with the loop component 28 to releasably hold the body 12 in position about the arm of the patient. Of course, to release the bladder cover 10 and the bladder 22 therein, from the arm of the patient, the hook component 30 is simply pulled from the loop component 28, and the body 12 of the cover is removed from the arm.

Figure 7:
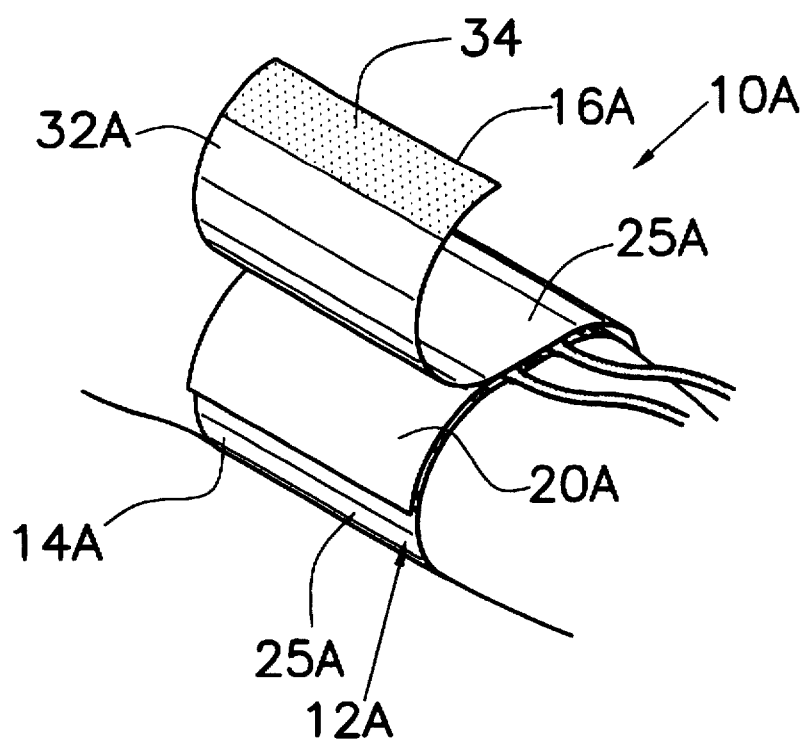
FIG. 7 illustrates a perspective view of the first alternate embodiment of the bladder cover of the present invention as it is received about an appendage of a patient.

In FIGS. 6 and 7 an alternate embodiment of the bladder cover of the present invention is illustrated generally at 10A. For convenience, features and components of the bladder cover 10A which are common to the above-described cover 10 are referenced with common numerals followed by the alphabetic character "A".

As illustrated, the bladder cover 10A includes an alternate mechanism for releasably securing the elongated portion 14A of the body 12A about an appendage of a patient. In this regard, the mechanism includes a third adhesive surface portion 34 disposed on the second surface 32A of the elongated portion 14A proximate the first end portion 16A. Thus, as illustrated in FIG. 7, when the elongated portion 14A is wrapped around the appendage of the patient, the third adhesive surface portion 34 is in position to be releasably secured to the first surface 25A of the elongated portion 14A in order to secure the cover 10A on the arm of the patient. Further, in the preferred embodiment at least a portion of the first surface 25A is covered with a relatively non-porous material to provide a bonding surface which allows the third adhesive surface portion 34 to be repetitively secured and removed from engagement with the first surface 25A. In this regard, in one embodiment the body 12A is fabricated of a two-ply material, having a first layer of a soft, absorbent material and a thin second layer of relatively soft, flexible, plastic film which is substantially fluid impervious and which forms the first surface 25A. One suitable two-ply material is a spun bond polypropylene with film, currently being sold by Poly-Bond, Inc., of Charlotte, N.C. This Poly-Bond tissue has the desired fluid impervious qualities and is inexpensive, such that the bladder cover 10A can be cost effectively used as a disposable item.

Figure 8:
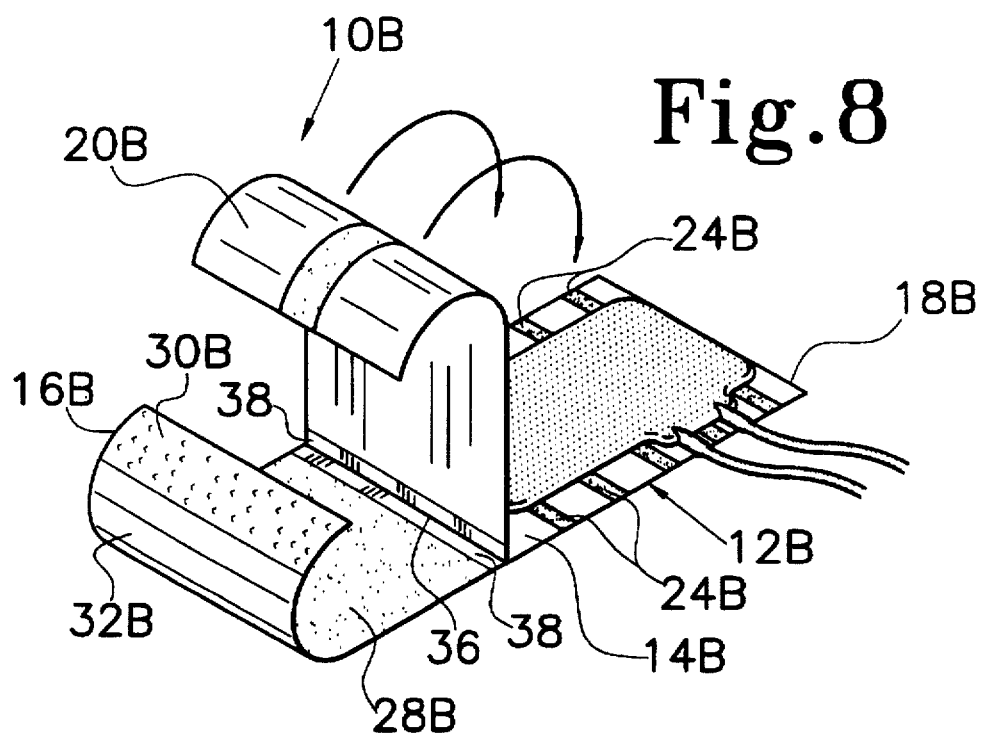
FIG. 8 illustrates a perspective view of a second alternate embodiment of bladder cover of the present invention.

A second alternate embodiment of the bladder cover of the present invention is illustrated generally at 10B in FIG. 8. For convenience, features and components of the bladder cover 10B which are common to the above-described cover 10 are referenced with common numerals followed by the alphabetic character "B".

As illustrated, the edge portion 36 of the flap portion 20B of the bladder cover 10B is secured to the elongated portion 14B transversely such that the flat portion 20B pivots in a longitudinal direction to cover a bladder 22 which has been secured to the elongated portion 14B. Further, in the illustrated embodiment the flap portion 20B is releasably secured to the elongated portion 14B with an adhesive strip 38. However, it will be recognized that other means could be used for releasably securing the flap portion 20B to the elongated portion 14B, such as a hook and loop fastener. Further, the flap portion 20B can be permanently secured to the elongated portion 14B if desired.

Figure 9:
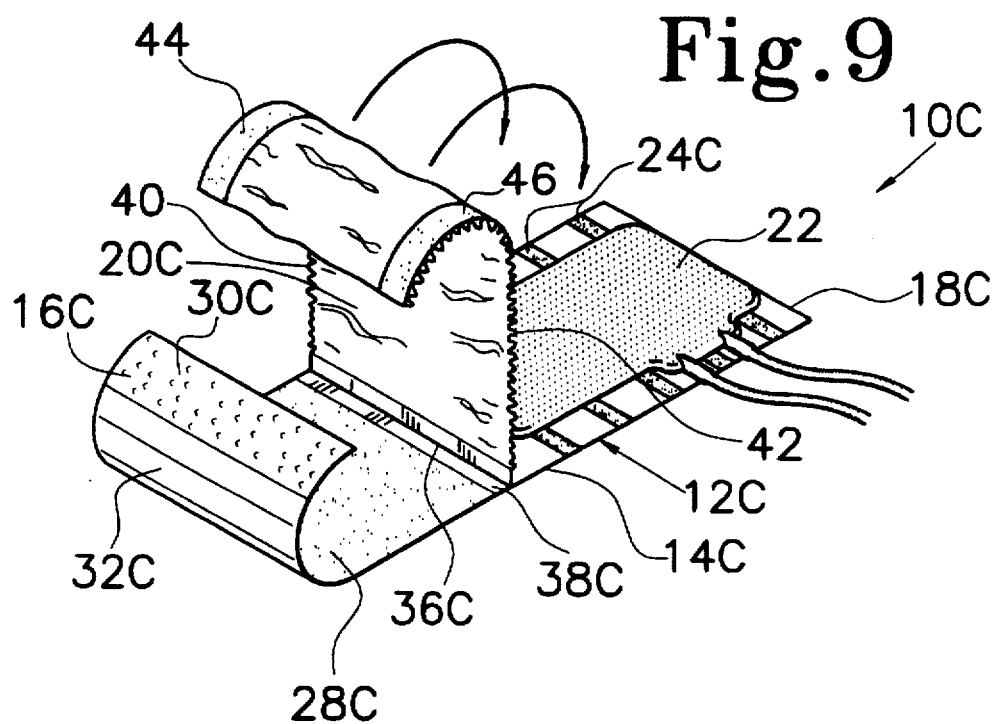
FIG. 9 illustrates a perspective view of a third alternate embodiment of the bladder cover of the present invention.

A second alternate embodiment of the bladder cover of the present invention is illustrated generally at 10C in FIG. 9. For convenience, features and components of the bladder cover 10C which are common to the above-described covers 10 and 10B are referenced with common numerals followed by the alphabetic character "C".

As with the cover 10B, the edge portion 36C of the flap portion 20C of the bladder cover 10C is secured to the elongated portion 14C transversely such that the flap portion 20C pivots in a longitudinal direction to cover a bladder 22 which has been secured to the elongated portion 14C. However, it will be noted that the material of the flap portion 32 is gathered at the edge portions 40 and 42 causing a blousing of the material of the flat portion 20C between the edge portions 40 and 42. This blousing of the material of the flap portion 20C insures that ample room is provided between the flap portion 20C and the elongated portion 14C to allow for the inflation of the bladder 22. Accordingly, the protective cover 10C does not interfere with the operation of a sphygmomanometer bladder. Further, adhesive strips 44 and 46 can be provided to releasably hold the flap portion 20C in position over the bladder 22 if desired.

In light of the above, it will be recognized that the bladder cover of the present invention has many advantages over the prior art. The bladder covers 10, 10A, 10B and 10C obviate the need for a permanent cover or cuff over a medical bladder, and substantially reduce the risk of contaminates being communicated between the patient and the medical bladder. Should a cover of the present invention be contaminated with bodily fluids, or other contaminants, during use it can simply be replaced with a new cover. Further, the cover of the present invention is inexpensive to manufacture and easy to use. While a preferred embodiment has been shown and described, it will be understood that there is no intent to limit the invention to such disclosure, but rather it is intended to cover all modifications and alternate constructions falling within the spirit and scope of the invention as defined in the appended claims.

I claim:

1. A medical bladder cover for releasably securing a medical bladder to a patient and for providing a protective covering around the medical bladder, said bladder cover comprising:

a body fabricated of flexible sheet material, said body including an elongated portion for being releasably received around an appendage of a patient, said elongated portion having first and second end portions and first and second surfaces, and having a bladder engaging portion for releasably engaging a medical bladder, said body also including a flap portion secured to said elongated portion for being folded over the medical bladder as said elongated portion engages said medical bladder;

a first securement device for releasably securing said body to the medical bladder, said first securement device including a plurality of first adhesive surface portions provided on said bladder engaging portion of said elongated portion of said body for releasably bonding said bladder engaging portion to the medical bladder; and a second securement device for releasably securing said elongated portion of said body about the appendage of the patient.

2. The medical bladder cover of claim 1 wherein said first securement device includes at least one second adhesive surface portion provided on said flap portion of said body for releasably bonding said flap portion to said medical bladder.

3. The medical bladder cover of claim 1 wherein said second securement device includes a hook and loop fastener.

4. The medical bladder cover of claim 3 wherein said hook and loop fastener includes a loop component disposed on said first surface of said elongated portion of said body and a hook component disposed on said second surface of said elongated portion of said body.

5. The medical bladder cover of claim 1 wherein said flap portion extends laterally from a longitudinal edge of said elongated portion of said body.

6. A medical bladder cover for releasably securing a medical bladder to a patient and for providing a protective covering around the medical bladder, said bladder cover comprising:

a body fabricated of flexible sheet material, said body including an elongated portion for being releasably received around an appendage of a patient, said elongated portion having first and second end portions and first and second surfaces, and having a bladder engaging portion for releasably engaging a medical bladder, said body also including a flap portion defining a first edge portion secured transversely across said elongated portion of said body so as to pivot in a longitudinal direction to cover said bladder engaging portion of said elongated portion as said elongated portion engages said medical bladder;

a first securement device, said first securement device including at least one first adhesive surface portion provided on said bladder engaging portion of said elongated portion of said body for releasably bonding said bladder engaging portion to the medical bladder; and a second securement device.

7. The medical bladder cover of claim 6 wherein said flap portion defines second and third opposite edge portions proximate which said flexible sheet material of said flap portion is gathered causing a blousing of said flap portion whereby space is provided between said flap portion and said elongated portion to accommodate the positioning of a medical bladder.

8. The medical bladder cover of claim 6 wherein said flap portion defines second and third opposite edge portions proximate which said flexible sheet material of said flap portion is gathered causing a blousing of said flap portion whereby space is provided between said flap portion and said elongated portion to accommodate the positioning of a medical bladder.

9. A medical bladder cover for releasably securing a medical bladder to a patient and for providing a protective covering around the medical bladder, said bladder cover comprising:

a body fabricated of flexible sheet material, said body including an elongated portion for being releasably received around an appendage of a patient, said elongated portion having first and second end portions and first and second surfaces, and having a bladder engaging portion for releasably engaging a medical bladder, said body also including a flap portion secured to said elongated portion for being folded over the medical bladder as said elongated portion engages said medical bladder;

a first securement device for releasably securing said body to the medical bladder, said first securement device including at least one first adhesive surface portion provided on said bladder engaging portion of said elongated portion of said body for releasably bonding said bladder engaging portion to the medical bladder; and a second securement device for releasably securing said elongated portion of said body about the appendage of the patient, said second securement device including a second adhesive surface portion provided on said second surface of said elongated portion of said body proximate said first end portion of said elongated portion.

10. The medical bladder cover of claim 9 wherein said flap portion extends laterally from said longitudinal edge of said elongated portion of said body proximate said second end portion of said elongated portion whereby said body defines an L-shaped configuration.

11. A medical bladder cover for releasably securing a medical bladder to a patient and for providing a protective covering around the medical bladder, said bladder cover comprising:

a body fabricated of flexible sheet material, said body including an elongated portion for being releasably received around an appendage of a patient, said elongated portion having first and second end portions and first and second surfaces, and having a bladder engaging portion for releasably engaging a medical bladder, said body also including a flap portion secured to said elongated portion for being folded over the medical bladder as said elongated portion engages said medical bladder;

a first segment device for releasably securing said body to the medical bladder, said first securement device including at least one first adhesive surface portions provided on said bladder engaging portion of said elongated portion of said body for releasably bonding said bladder engaging portion to the medical bladder, said first securement device further including at least one second adhesive surface portion provided on said flap portion of said body for releasably bonding said flap portion to said medical bladder; and a second securement device for releasably securing said elongated portion of said body about the appendage of the patient.

* * * * *